United States Patent
Kim

(10) Patent No.: US 9,776,045 B2
(45) Date of Patent: *Oct. 3, 2017

(54) CARBOXYLIC BRANCHED CHAIN-CUTTING AGENT FOR GOLF BALL-COVERING IONOMER RESIN, GOLF BALL COATING COMPOSITION, AND METHOD FOR MANUFACTURING GOLF BALL

(71) Applicant: Qingdao Fantom Golf Co., Ltd, Shandong (CN)

(72) Inventor: Ki Jung Kim, Busan (KR)

(73) Assignee: QINGDAO FANTOM GOLD CO., LTD., Shandong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/908,657

(22) PCT Filed: Jul. 29, 2014

(86) PCT No.: PCT/KR2014/006925
§ 371 (c)(1),
(2) Date: Jan. 29, 2016

(87) PCT Pub. No.: WO2015/016570
PCT Pub. Date: Feb. 5, 2015

(65) Prior Publication Data
US 2016/0166885 A1 Jun. 16, 2016

(30) Foreign Application Priority Data
Jul. 29, 2013 (KR) .......... 10-2013-0089480

(51) Int. Cl.
| | |
|---|---|
| *A63B 45/00* | (2006.01) |
| *A63B 37/00* | (2006.01) |
| *C09D 7/12* | (2006.01) |
| *C08K 5/3412* | (2006.01) |
| *C09D 5/00* | (2006.01) |
| *C07D 203/08* | (2006.01) |
| *C08K 5/10* | (2006.01) |
| *C08K 3/00* | (2006.01) |

(52) U.S. Cl.
CPC .......... *A63B 37/0022* (2013.01); *A63B 45/00* (2013.01); *C07D 203/08* (2013.01); *C09D 5/00* (2013.01); *C09D 7/1233* (2013.01); *C08K 3/0033* (2013.01); *C08K 5/10* (2013.01); *C08K 5/3412* (2013.01)

(58) Field of Classification Search
None
See application file for complete search history.

(56) References Cited

U.S. PATENT DOCUMENTS

| | | | |
|---|---|---|---|
| 4,749,617 A * | 6/1988 | Canty | B32B 27/04 428/332 |
| 5,506,004 A | 4/1996 | Maruoka et al. | |
| 5,823,889 A | 10/1998 | Aoyama et al. | |
| 5,895,105 A | 4/1999 | Nesbitt et al. | |
| 6,015,356 A | 1/2000 | Sullivan | |
| 6,365,679 B1 * | 4/2002 | Crast | A63B 37/0003 473/351 |
| 6,383,644 B2 | 5/2002 | Fuchs | |
| 6,454,667 B1 * | 9/2002 | Iwami | A63B 37/0003 473/351 |
| 6,878,075 B2 | 4/2005 | Kim | |
| 7,824,739 B2 | 11/2010 | Fujisawa | |
| 8,003,176 B2 | 8/2011 | Ylitalo et al. | |
| 2004/0144224 A1 * | 7/2004 | Yamakawa | B24B 21/02 83/13 |
| 2006/0035724 A1 | 2/2006 | Watanabe et al. | |
| 2006/0189733 A1 | 8/2006 | Kennedy et al. | |

(Continued)

FOREIGN PATENT DOCUMENTS

| | | |
|---|---|---|
| EP | 062338 | * 10/1982 |
| JP | 2000-140159 | 5/2000 |

(Continued)

OTHER PUBLICATIONS

Menadiona Technical Data Sheet for Crosslinker CL-467 (no date).*
International Search Report dated Dec. 1, 2014 for International application No. PCT/KR2014/006927.
International Search Report dated Nov. 28, 2014 for corresponding International application No. PCT/KR2014/006925.
Thain, Eric Science and Golf IV (2002); pp. 319-327, Chapter 28, "Compression by Any Other Name".
Furukawa et al. (1973) Polymer Journal vol. 5 No. 3, pp. 231-242, "Equibinary (cis-1,4-1,2)Polybutadiene".

*Primary Examiner* — David Buttner
(74) *Attorney, Agent, or Firm* — Swanson & Bratschun, L.L.C.

(57) ABSTRACT

The present invention relates to a carboxylic branched chain-cutting agent for a golf ball-covering ionomer resin, a golf ball coating composition, and a method for manufacturing a golf ball. The present invention can provide a coating composition containing within an appropriate range, a specific compound for use as a carboxylic branched chain-cutting agent for a golf ball-covering ionomer resin, and thus can provide a golf ball on which a bridge is formed between a golf ball covering resin and a coating resin. By providing the coating composition containing a specific composition for use as a carboxylic branched chain-cutting agent for a golf ball-covering ionomer resin, the present invention is appropriate for ensuring the physical properties of the golf ball, such as yellowing resistance, and workability, such as pot life, even eliminating an adhesion pretreatment step, thereby reducing side effects due to the existing pretreatment step while providing a golf ball having excellent physical properties.

6 Claims, 1 Drawing Sheet

(56) References Cited

U.S. PATENT DOCUMENTS

| | | |
|---|---|---|
| 2010/0227945 A1 | 9/2010 | Bissinger |
| 2011/0244983 A1* | 10/2011 | Shen ............... A63B 37/0003 |
| | | 473/371 |
| 2012/0309560 A1 | 12/2012 | Sullivan et al. |
| 2016/0166888 A1* | 6/2016 | Kim .................. A63B 37/003 |
| | | 473/377 |

FOREIGN PATENT DOCUMENTS

| | | |
|---|---|---|
| JP | 2008-161582 | 7/2008 |
| KR | 10-1998-0070080 | 10/1998 |
| KR | 10-0303195 | 12/2001 |
| KR | 10-2006-0016105 | 2/2006 |
| WO | WO 00/04072 | 1/2000 |

* cited by examiner

| Classification | Surface of cross-cut areas from which listing has occurred. (Example for six parallel cuts). | Rate of adhesion |
|---|---|---|
| 5B | none | The edges of the cuts are completely smooth, none of the squares or the lattice are detached. |
| 4B | 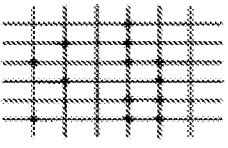 | Small flakes of coating are detached at intersections; less than 5% of the area is affected. |
| 3B | 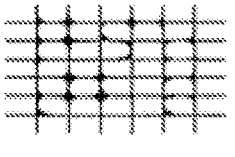 | Small flakes of coating are detached along edges and at intersections of cuts. The area affected is 5 to 15% of the lattice. |
| 2B | 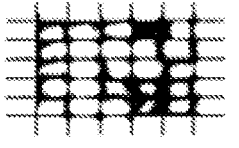 | The coating has flaked along the edges and at parts of the squares. The affected area is 15 to 25% of the lattice. |
| 1B | 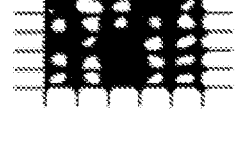 | The coating has flaked along the edges of the cuts in large ribbons and entire squares have detached. The area affected is 35 to 65% of the lattice. |
| 0B | Flaking and detachment in excess of 65% | |

CARBOXYLIC BRANCHED CHAIN-CUTTING AGENT FOR GOLF BALL-COVERING IONOMER RESIN, GOLF BALL COATING COMPOSITION, AND METHOD FOR MANUFACTURING GOLF BALL

RELATED APPLICATIONS

This application is a National Stage Entry of International Application No. PCT/KR2014/006925 filed on Jul. 29, 2014, and claims the benefit of Korean Application No. 10-2013-0089480, filed on Jul. 29, 2013, which are hereby incorporated by reference in its entirety for all purposes as if fully set forth herein.

TECHNICAL FIELD

The present invention relates to a carboxylic branched chain cleavage agent of a golf ball cover ionomer resin, a golf ball coating composition, and a method for manufacturing a golf ball, and more particularly, to a golf ball coating composition containing a carboxylic branched chain cleavage agent of a golf ball cover ionomer resin within a suitable content range and to a golf ball having a bridge structure between a golf ball cover resin and a coating resin, which is manufactured using the coating composition.

BACKGROUND ART

A golf ball comprises a core and a cover surrounding the core. In a conventional method for manufacturing the golf ball, a core material is kneaded, rolled out thin like a piece of paper, compressed, cut to have a core size, and then imprinted any spherical core shape. Next, the spherical core is covered with a cover in a mold, thereby manufacturing the so-called two-piece golf ball. This process may be repeated to manufacture a three-piece golf ball, a four-piece golf ball, a five-piece golf ball or the like.

Thereafter, the mold seam of the golf ball is polished, and the golf ball is marked with a logo and coated with a coating material, followed by drying, thereby obtaining a commercially available golf ball.

Herein, materials for the golf ball cover, particularly an ionomer resin that has recently been frequently used exhibits excellent properties required for golf balls, but has poor adhesion to other materials. To make up this disadvantage, pretreatment step for improving various adhesion property (hereinafter referred to as the "adhesion pretreatment step" or "primer coating step") are performed after grinding. Examples of the adhesion pretreatment step include any primer coating followed by near infrared ray (NIR) drying, plasma irradiation, corona discharge treatment, etc.

Such pretreatment or step cost a great deal due to the purchase, maintenance and management of expensive equipment, the purchase of primer coatings, labor costs, etc., cause environmental problems and process losses, and also involve difficulties in control, including any environmental problems, increased process failure rates and poor quality problems.

BRIEF DESCRIPTION OF THE DRAWING

FIG. 1 shows various degrees of removal of the cross-cutting test.

DISCLOSURE

Technical Problem

The present invention has been made in order to solve the problems, and it is an object of the present invention to provide a carboxylic branched chain cleavage agent of a golf ball cover ionomer resin, which makes it possible to ensure workability such as pot life while maintaining adhesion property, yellowing resistance or the like by a single-step coating process omitted an adhesion pretreatment step, having the same level or similar to that of a conventional product performing the adhesion pretreatment step, to provide a golf ball coating composition comprising the carboxylic branched chain-cutting agent.

It is another object of the present invention to provide a method for manufacturing the golf ball, and a golf ball which is manufactured using the coating composition of the present invention.

Technical Solution

In order to accomplish the above object, the present invention provides a carboxylic branched chain cleavage agent of a golf ball cover ionomer resin, which comprises a compound represented by the following formula 1:

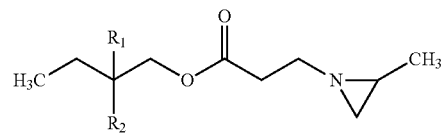

Formula 1 wherein $R_1$ and $R_2$ are each independently selected from H, $C_1$-$C_{10}$ alkyl, $C_5$-$C_{15}$ aralkyl, $C_6$-$C_{16}$ aryl, and

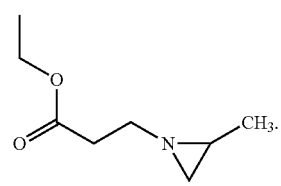

The present invention also provides a top coating composition for a golf ball, comprising said carboxylic branched chain cleavage agent of a golf ball cover ionomer resin and coating resin.

The present invention also provides a method for manufacturing a golf ball, comprising the steps of: manufacturing a golf ball core, manufacturing a cover surrounding the core, grinding the mold seam of the cover, an adhesion pretreatment onto the surface of the cover, a top coating, and a drying, wherein the step of the top coating use the coating composition, and the step of the adhesion pretreatment onto the surface of the cover is omitted.

The present invention also provides a golf ball which is manufactured by the method and has a coating layer onto the surface of the dimple parts of the cover, wherein the coating layer has a structure in which a bridge is formed between a cover resin constituting the dimple parts of the golf ball and the coating resin.

Hereinafter, the present invention will be described in detail.

The present invention has a technical feature of providing a specific compound as the carboxylic branched chain cleavage agent of a golf ball cover ionomer resin.

For reference, the term of "the carboxylic branched chain cleavage agent of a golf ball cover ionomer resin", as used herein, unless otherwise specified, refers to a component that is contained in the coating composition and that has a role of cleaving the branched chain carboxyl group (—COOH) of the golf ball cover ionomer resin. The carboxylic branched chain cleavage agent exhibits the effect of producing active sites for molecular bond of the coating resin on the surface of the golf ball cover ionomer resin.

As a specific example, the present invention may provide a carboxylic branched chain-cleavage agent of a golf ball cover ionomer resin, which comprises a compound represented by the following formula 1:

Formula 1

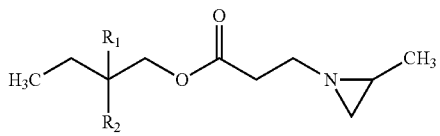

wherein $R_1$ and $R_2$ are each independently selected from the group consisting of H, $C_1$-$C_{10}$ alkyl, $C_5$-$C_{15}$ aralkyl, $C_6$-$C_{16}$ aryl, and

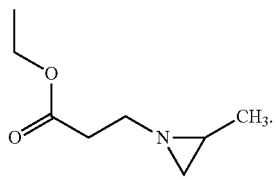

As another example, the carboxylic branched chain cleavage agent for the golf ball cover ionomer resin may be a compound represented by the following formula 2 or comprises the same.

Formula 2

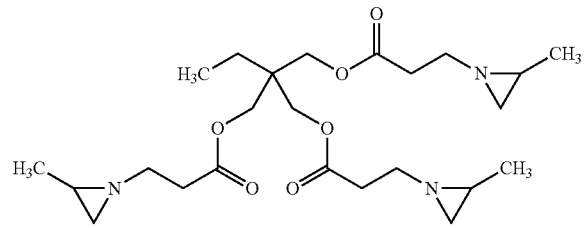

If required, the carboxylic branched chain cleavage agent of the golf ball cover ionomer resin may additionally include one or more selected from the group consisting of an ethyleneimine-based crosslinker, a propyleneimine-based crosslinker, a blocked aziridine crosslinker, and the like.

Examples of the ethyleneimine-based crosslinker include trade name CL-422 and CL-427, etc., available from Menadiona S. A.; examples of propyleneimine-based crosslinker include trade name CL-467, XAMA-2, XAMA-7 and XAMA-220, etc., available from Menadiona S. A.; and examples of the blocked aziridine crosslinker include trade name POLY-U25 available from Menadiona S. A., and trade name SU-125F available from Meisei, etc.

As an example, the additional components may be used in an amount of 1 to 150 parts by weight, 5 to 100 parts by weight, or 10 to 50 parts by weight, based on 100 parts by weight of the chain cleavage agent comprising the compound represented by the above formula 1 or the chain cleavage agent comprising the compound represented by the above formula 2.

As a specific example, the additional components may be used in an amount of 1 to 150 parts by weight, 5 to 100 parts by weight, or 10 to 50 parts by weight, based on 100 parts by weight of the compound represented by the above formula 1 or the compound represented by the above formula 2.

The golf ball cover ionomer resin may be, for example, one or more selected from the group consisting of a hard ionomer which is a magnesium, lithium, sodium or zinc salt of a copolymer of a $C_2$-$C_8$ olefin with a $C_3$-$C_8$ unsaturated monocarboxylic acid and has a modulus of 30,000 to 55,000 P.S.I., and a soft ionomer which is a magnesium, lithium, sodium or zinc salt of a copolymer of a $C_2$-$C_8$ olefin with a $C_2$-$C_{22}$ acrylate ester-based unsaturated monomer and has a modulus of 3,000 to 7,000 P.S.I.

As a specific example, the golf ball cover ionomer resin may be one or more selected from the group consisting of a hard ionomer which is a magnesium, lithium, sodium or zinc salt of a copolymer of ethylene with methacrylic acid, and a soft ionomer which is a sodium salt of a terpolymer of n-butyl acrylate or iso-butyl acrylate, ethylene and methacrylic acid.

According to the present invention, a coating composition may comprise the carboxylic branched chain cleavage agent of the golf ball cover ionomer resin, which makes it possible to eliminate any pretreatment step to be performed prior to the formation of a coating layer onto the surface of the dimple part of a golf ball in this art.

Specifically, a top coating composition for a golf ball according to the present invention may comprise the carboxylic branched chain cleavage agent of the golf ball cover ionomer resin and the coating resin.

The carboxylic branched chain cleavage agent of the golf ball cover ionomer resin may be used as the amount of, for example, 1 to 3.5 parts by weight, 1.5 to 3 parts by weight, or 1.5 to 2.5 parts by weight, based on 100 parts by weight of the coating resin.

The above range is determined considering both the adhesion property and pot life of the coating composition. Under the lower limit of the above range, the pot time (curing rate) will be slow, but the adhesion property may be poor, and over the upper limit of the above range, the adhesion property may be improved, but the pot time (curing rate) will be shortened and thus resulting in a reduced workability of the coating composition.

For reference, the term of "pot time", as used herein, unless otherwise specified, refers to the time required for normal coating after mixing of a base resin and a curing agent in a two-component coating composition. When the suitable pot time is passed, the coating composition may change as any gel type and thus it is impossible to be spray-coated.

The carboxylic branched chain cleavage agent of the golf ball cover ionomer resin contained in the coating composition, may serve to have a role of form a bridge between the cover resin of the golf ball and the coating resin of the golf ball.

For reference, the term of "bridge", as used herein, refers to differ principally from a cross-linking. Specifically, unless otherwise specified, the term of "bridge", as used herein, refers to cleaving a —COOH group in the branched chain of the golf ball cover resin and performing any molecular bond between the cleaved —COOH group and the golf ball coating resin, thereby providing the effect of improving the adhesion property of the coated golf ball.

For reference, the term of "crosslinking", as usually used, refers to form a three-dimensional structure in a coating resin itself and structurally differs from the bridge used herein.

The coating resin, for example may be selected from the group consisting of a two-component urethane resin, a two-component acrylic urethane resin, and a PVC resin. As a specific example, the coating resin may be a two-component acrylic urethane resin composed of an acryl-urethane base resin and an isocyanate curing agent.

If the coating resin is a two-component resin, the base resin and the curing agent may be blended, and then introduced separately. The curing agent may be used in an amount of 30 to 60 parts by weight, or 45 to 55 parts by weight, based on 100 parts by weight of the base resin.

In addition, the composition may further include a pigment in an amount of 1 to 10 parts by weight, or 1 to 5 parts by weight, based on total 100 parts by weight of the composition. Herein, the pigment may be any pigment that is generally used in the golf ball related arts. As an example, the pigment may be one or more selected from titanium dioxide, barium sulfide, zinc oxide and zinc sulfide.

A method for manufacturing a golf ball according to the present invention comprises the steps of: manufacturing a golf ball core, manufacturing a cover surrounding the core, grinding the mold seam of the cover, an adhesion pretreatment onto the surface of the cover, a top coating, and a drying, wherein the step of the top coating use the coating composition, and the step of the adhesion pretreatment onto the surface of the cover is omitted.

For reference, the step of the adhesion pretreatment onto the surface of the cover may be performed by a primer coating followed by a near infrared (NIR) drying step, a plasma discharge treatment step, or a corona discharge treatment step.

The core may be prepared by butadiene rubber, or a mixture of various additional resins and additives, if required.

Examples of the additives include Zinc Diacrylate, Zinc Oxide, Barium Sulfate, Titanium Dioxide, Zinc Stearate, Peroxide, Ground Flash, Penta-ChloroThioPhenol, Antioxidants, etc.

Prior to the step of the top coating, a step of marking may be further performed according to a conventional method in this art.

In addition, in the step of manufacturing the cover, one to four cover over-layers may be overlapped around the core to provide two-piece to five-piece golf balls. Further, the outermost cover layer may be manufactured to have dimple parts having various shapes.

The step of the top coating may be performed according to a conventional method in this art. For example, the step of the top coating may be performed by air-spray coating, electrostatic coating, or the like.

The step of the drying may also be performed according to a conventional method in this art. For example, it may be performed by thermal drying, near infrared (NIR) drying, or hot-air drying.

For reference, the step of manufacturing the golf ball core, the step of manufacturing the cover surrounding the core, the step of grinding the mold seam of the cover, the step of the adhesion pretreatment onto the surface of the cover, the step of the label marking, the step of the top coating, and the step of the drying, are not specifically limited and may be performed by conventional methods in this arts.

According to said method of the present invention, there may be provided a golf ball having a coating layer onto the surface of the dimple parts of the golf ball, wherein the coating layer has a structure in which a bridge is formed between a cover resin constituting the dimple parts of the golf ball and the coating resin.

Herein, the coating layer may have a coating thickness in the range of, for example, 5 to 50 μm, 10 to 30 μm, or 15 to 25 μm.

The golf ball according to the present invention can exhibit adhesion property (cross-cutting test, air-cannon test, and sand abrasion test) and yellowing resistance properties with the same or similar to those of primer coated, even though it is omitted to a conventional primer coating step. In addition, the pot life of the coating composition is in a suitable range in terms of ensuring workability.

Advantageous Effects

According to the present invention, the coating composition is provided which comprises a specific compound as a carboxylic branch cleavage agent of the golf ball cover ionomer resin. The coating composition of the present invention is advantageous in terms of ensuring not only golf ball properties such as adhesion property and yellowing resistance properties, but also workability such as pot life, even when the step of the adhesion pretreatment is omitted. Thus, according to the present invention, a golf ball having excellent physical properties can be provided while side effects caused by a the adhesion pretreatment step may be reduced.

MODE FOR INVENTION

Hereinafter, preferred examples will be presented for a better understanding of the present invention. It is to be understood, however, that these examples are for illustrative purposes only and are not intended to limit the scope of the present invention.

The components used in the following examples and comparative examples are as follows.

1) Core of the golf ball: butadiene rubber (manufactured by LG Chemical Ltd.; trade name: BR1208);

2) Resin of cover of the golf ball cover: hard ionomer (manufactured by DuPont; trade name: Surlyn);

3) Coating resin of the golf ball: two-component urethane resin (acrylic urethane (PPG) as a base resin; and isocyanate (PPG) as a curing agent);

4) Carboxylic branched chain cleavage agent of golf ball cover ionomer resin: compound represented by the following formula 2:

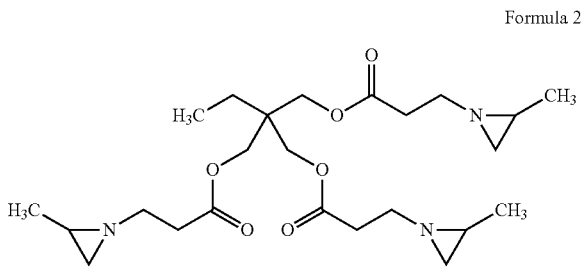

Formula 2

In addition, a water-soluble primer paint (urethane-based paint; PPG) was prepared as a primer for a primer coating (corresponding to the adhesion pretreatment) used in Comparative Example 1.

Example 1: Use of 2 Parts by Weight of Compound of Formula 2

Preparation of Golf Ball Coating Composition

From, the above components, coating compositions were prepared according to the mixing ratio shown in below Table 1. Specifically, a base resin and a curing agent were blended with each other, and then 2 parts by weight of the compound of formula 2 was added to the blend.

Separately from the coating composition, a spherical core was prepared from 100 percents by weight of butadiene rubber, and a hard ionomer as a cover resin was once injection-molded onto the core, after which the mold seam of the cover was grinded, thereby preparing a two-piece golf ball.

Each of the prepared coating compositions was spray-coated onto the two-piece golf ball to provide thick coating layer having a thickness of 20 μm, and then the coating layer was dried by near infrared rays (NIR) (coating layer has a thickness of 10 to 20 μm).

It could be seen that the coating layer formed onto the surface of the dimple parts of the prepared golf ball had bridged structure formed between the dimple parts of the golf ball and the coating resin.

The physical properties of the prepared golf ball were measured using the test methods described below, and the results of the measurement are summarized in Table 1 below.

Example 2: Use of 3 Parts by Weight of Compound of Formula 2

A golf ball was prepared according to the same process as described in Example 1, except that the compound of formula 2 was used in an amount of 3 parts by weight. The physical properties of the prepared golf ball were measured in the same manner as described in Example 1, and the results of the measurement are summarized in Table 1 below.

Comparative Example 1: Application of Coating without any Compound of Formula 2 after Primer Coating A golf ball was prepared according to the same process as described in Example 1, except that it was coated with the primer for the primer coating and then dried by near infrared rays (NIR) (corresponding to the adhesion pretreatment) prior to the two-piece golf ball was coated directly with the coating composition, and then was coated directly with a coating composition without any the compound of formula 2. The physical properties of the prepared golf ball were measured in the same manner as described in Example 1, and the results of the measurement are summarized in Table 1 below.

Comparative Example 2: Use of 4 Parts by Weight of Compound of Formula 2

A golf ball was prepared according to the same process as described in Example 1, except that the compound of formula 2 was used in an amount of 4 parts by weight. The physical properties of the prepared golf ball were measured in the same manner as described in Example 1, and the results of the measurement are summarized in Table 1 below.

Measurement Means

Adhesion Property Test

1) Cross-Cutting Test: it was performed in accordance with ASTM D 3359.

Specifically, lines were drawn horizontally and vertically on the coated surface of the golf ball at 1.0-mm intervals with a cutter knife to form cross-cut patterns, and a tape was applied strongly to the cross-cut patterns and then quickly removed once. The degree of coating removal was rated on a scale of 0 B to 5 B based on the table in FIG. 1, with 5 B indicating the highest adhesion property.

2) Air-Cannon Test: the adhesion property of coating was tested by repeatedly hitting a ball to a metal plate at a distance of 1.5 meters at a speed of 40 m/s using a durability testing system. When coating was peel off after 60 hits, it was read to be poor. Adhesion was rated on a scale of 5 (excellent) to 0 (poor).

3) Sand Abrasion Test: a sample golf ball and grindstone were placed into a 10-liter cylindrical tube (rotating rpm conditions: 60 to 120) and rotated for 8 hours. The adhesion property of coating was rated on a scale of 0 (poor) to 5 (excellent).

4) Yellowing (Delta E, ΔE): a sample was exposed to the weather resistance tester QUV during 24 hours, and then the color of the sample was measured with a colorimeter. L, a and b values of the sample were calculated. Delta E, a scale of change in color, was calculated using the following equation. For reference, a higher Delta E value indicates a higher degree of yellowing.

$$\Delta E^* = [(\Delta L^*)^2 + (\Delta a^*)^2 + (\Delta b^*)^2]^{1/2} \quad \text{Equation}$$

5) Pot Life: The time (hrs) taken for becoming a gel which cannot be normally coated with the coating composition was measured.

TABLE 1

| | Adhesion Property | | | | |
| | Cross-Cutting | Air-Cannon | Sand Abrasion | Yellowing (ΔE) | Pot life |
|---|---|---|---|---|---|
| Example 1 | 5B | 5 | 5 | 1.15 | 3 hr |
| Example 2 | 5B | 5 | 5 | 1.21 | 2 hr |
| Comparative Example 1 | 5B | 5 | 5 | 1.17 | 8 hr |
| Comparative Example 2 | 4B | 4 | 4 | 1.24 | 30 min |

As can be seen in above Table 1, Examples 1 and 2 in which the carboxylic branched chain cleavage agent of the golf ball cover ionomer resin according to the present invention as coating suggests the same or similar as the effects for adhesion property, yellowing and pot time compared with the Comparative Example 1 in which the carboxylic branched chain cleavage agent of the golf ball cover ionomer resin as coating was not used. Thus, it was established that according to the present invention, a golf ball having excellent properties can be manufactured, even when the primer coating step is omitted.

Meanwhile, Comparative Example 2 in which the carboxylic branched chain cleavage agent of the golf ball cover ionomer resin was used in an amount larger than the amount specified in the present invention, suggests some poor adhesion property, yellowing and abrasion resistance, and pot life was also too fasted to represent impossible application in terms of workability.

The invention claimed is:

1. A method for manufacturing a golf ball, comprising the steps of: manufacturing a golf ball core, manufacturing an ionomer cover surrounding the core, grinding a mold seam of the cover, a top coating, and a drying, wherein the step of the top coating uses a top coating composition, wherein the method does not include a step of an adhesion pretreatment onto the surface of the cover, wherein the top coating composition comprises a carboxylic branched chain cleavage agent of a golf ball cover ionomer resin, a crosslinker and a coating resin, wherein the carboxylic branched chain cleavage agent comprises a compound represented by the following formula 1:

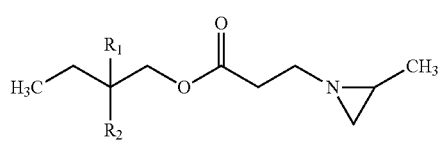

Formula 1 wherein R1 and R2 are each independently selected from the group consisting of H, $C_{1-10}$ alkyl, $C_5$-$C_{15}$ aralkyl, $C_6$-$C_{16}$ aryl, and

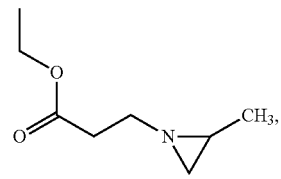

wherein the carboxylic branched chain cleavage agent comprises 1 to 3.5 parts by weight for 100 parts by weight of the coating resin and solvent, wherein the crosslinker is N,N'-(methylenedi-p-phenylene)bis(aziridine-1-carboxamide), as an amount of 1 to 150 parts by weight based on 100 parts by weight of the carboxylic branched chain cleavage agent of the golf ball cover ionomer resin, wherein the golf ball cover ionomer resin is one or more selected from the group consisting of a hard ionomer which is a magnesium, lithium, sodium or zinc salt of a copolymer of ethylene with methacrylic acid, and a soft ionomer which is a sodium salt of a terpolymer of n-butyl acrylate or iso-butyl acrylate, ethylene and methacrylic acid, wherein the coating resin is selected from the group consisting of a two-component urethane resin, a two-component acrylic urethane resin and a PVC resin, and wherein the drying step is performed by near infrared (NIR) drying.

2. The method of claim 1, further comprising a step of marking prior to the step of the top coating.

3. The method of claim 1, wherein the step of manufacturing the cover comprises a step of overlapping one to four cover over-layers around the core to provide two-piece to five-piece golf balls.

4. The method of claim 1, wherein the step of the top coating is performed by air-spray coating or electrostatic coating.

5. A golf ball which is manufactured by the method of claim 1, wherein the golf ball has a coating layer formed onto the surface of the golf ball, wherein the coating layer has a structure in which a bridge is formed between a cover resin constituting the surface parts of the golf ball and a coating resin.

6. The golf ball of claim 5, wherein the coating layer has a thickness of 5 to 50 μm.

* * * * *